United States Patent [19]

Kulick

[11] Patent Number: 5,425,355
[45] Date of Patent: Jun. 20, 1995

[54] ENERGY DISCHARGING SURGICAL PROBE AND SURGICAL PROCESS HAVING DISTAL ENERGY APPLICATION WITHOUT CONCOMITANT PROXIMAL MOVEMENT

[75] Inventor: Michael I. Kulick, San Francisco, Calif.

[73] Assignee: Laserscope, San Jose, Calif.

[21] Appl. No.: 646,948

[22] Filed: Jan. 28, 1991

[51] Int. Cl.⁶ .............................................. A61B 1/00
[52] U.S. Cl. .................................. 128/4; 604/22; 606/13; 606/14; 606/15; 606/16; 606/17
[58] Field of Search ................. 606/7, 10, 13–17, 606/170–171; 128/395, 397–398, 4, 749, 750–754; 604/96, 27, 22

[56] References Cited

U.S. PATENT DOCUMENTS

| | | | |
|---|---|---|---|
| 4,249,533 | 2/1981 | Komiya | 128/345 |
| 4,313,431 | 2/1982 | Frank | 606/14 |
| 4,564,180 | 1/1986 | Agee | . |
| 4,834,729 | 5/1989 | Sjostrom | . |
| 4,842,578 | 6/1989 | Johnson et al. | . |
| 4,962,770 | 10/1990 | Agee et al. | 606/170 |
| 4,963,147 | 10/1990 | Agee | . |
| 5,041,108 | 8/1991 | Fox et al. | 606/15 |
| 5,092,873 | 3/1992 | Simpson et al. | 606/170 |
| 5,217,434 | 6/1993 | Khoury | 606/7 |
| 5,246,436 | 9/1993 | Rowe | 606/13 |

FOREIGN PATENT DOCUMENTS 2639237 5/1990 France ........................... 606/15

OTHER PUBLICATIONS

3M Health Care Brochure, dated Oct. 1989, "Agee Inside Job Carpal Ligament Release System".
Sandzen, AFP, Nov. 1981, "Carpal Tunnel Syndrome".
Smith, Arch. Phys. Med. Rehabil. Sep. 1977, "Carpal Tunnel Syndrome".
MacDonald, Journal of Hand Surgery, undated, portion of article on Carpal Tunnel Syndrome.
Yamaguchi, et al., Minnesota Medicine, Jan. 1965, "Carpal Tunnel Syndrome".

*Primary Examiner*—Randall L. Green
*Assistant Examiner*—P. Zuttarelli
*Attorney, Agent, or Firm*—Banner, Birch, McKie & Beckett

[57] ABSTRACT

This invention relates to a surgical instrument. Specifically, a surgical instrument is disclosed which dispenses incising, transecting, or tissue treating energy to a body site or part undergoing an operation or treatment where energy is discharged from a conduit to effect the treatment. The disclosed instrument is inserted to an operative site that effectively rules out proximal manipulation of the instrument. Therefore, proximal insertion with subsequent distal manipulation excluding proximal side-to-side or up and down manipulation is disclosed. The disclosure further includes a deployable shield and is ideal for operative engagement to surgical sites on the body such as the carpal tunnel, tarsal tunnel, the wrist, temporomandibular joint, or scar tissue capsules forming around implants of the breast.

26 Claims, 8 Drawing Sheets

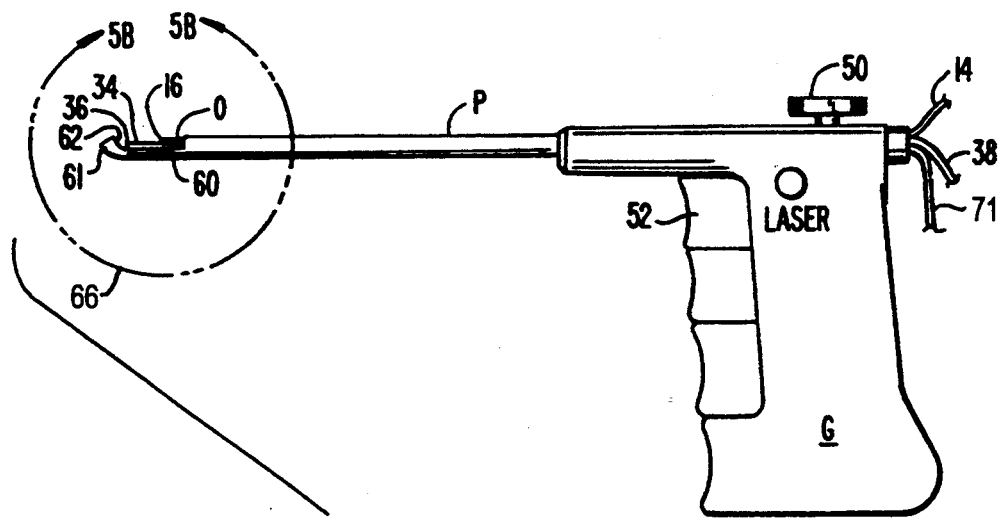
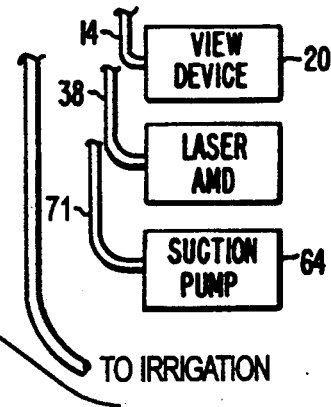
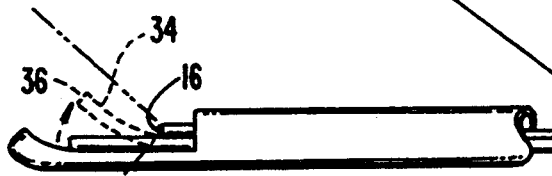
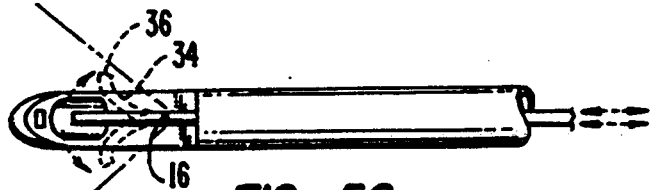
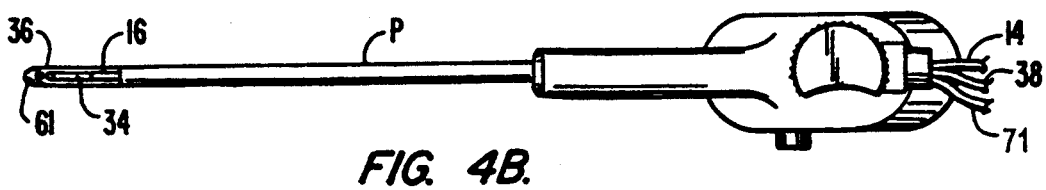
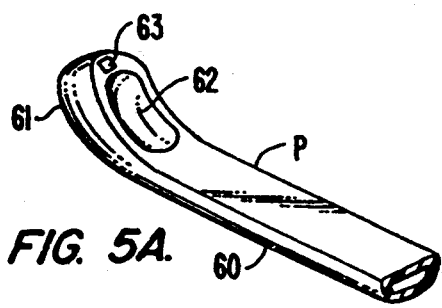
FIG. 4A.
FIG. 5B.
FIG. 5C.
FIG. 4B.
FIG. 5A.

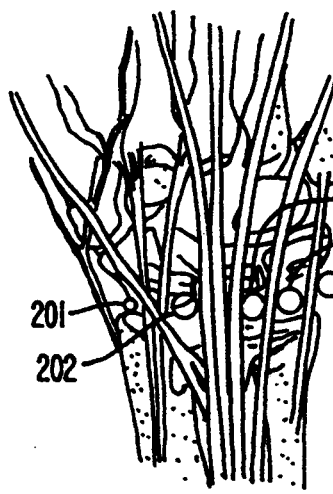 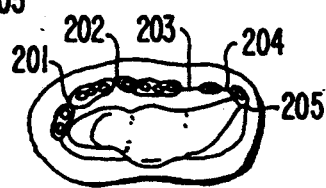 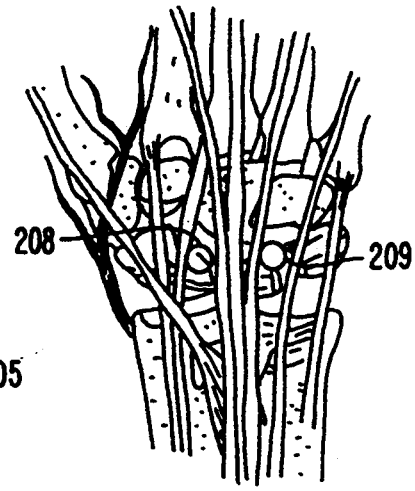
FIG. 11B.   FIG. 11A.   FIG. 11C.
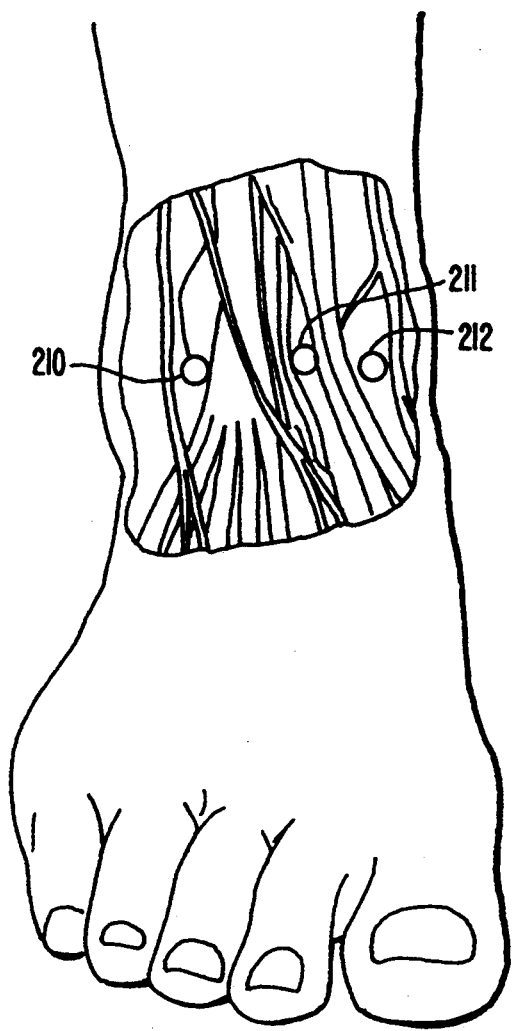 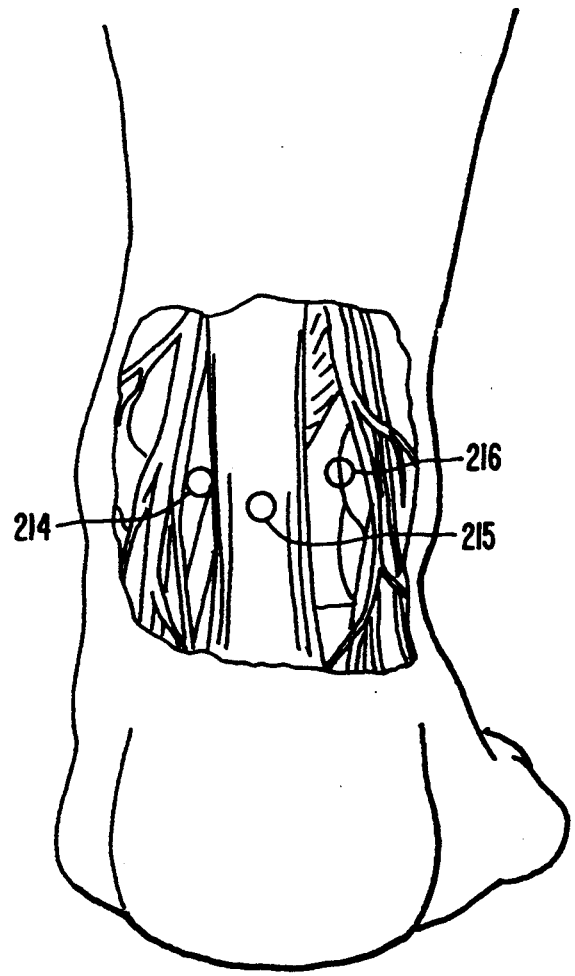
FIG. 12A.   FIG. 12B.

ENERGY DISCHARGING SURGICAL PROBE AND SURGICAL PROCESS HAVING DISTAL ENERGY APPLICATION WITHOUT CONCOMITANT PROXIMAL MOVEMENT

This invention relates to a surgical instrument. Specifically, a surgical instrument is disclosed which dispenses incising, transecting, or tissue-treating energy to a body site or part undergoing an operation or treatment where energy is discharged from the end of a conduit to affect the treatment. The disclosed instrument is inserted in an operative site that effectively rules out proximal manipulation of the instrument. Therefore, proximal insertion with subsequent distal manipulation excluding side-to-side proximal manipulation is disclosed. The disclosure further includes a deployable shield and is ideal for operative engagement to surgical sites on the body such as the carpal tunnel, tarsal tunnel, the wrist, elbow, ankle, temporomandibular joint, or scar tissue capsules forming around implants of the breast.

BACKGROUND OF THE INVENTION

Surgery accomplished with the use of energy discharging probes is well known. Examples of such energy discharging probes include surgical instruments operating upon the knee and laparoscopes for operative insertion into the abdomen. These instruments are all inserted into an incision and thereafter manipulated proximally (exterior of the patient) to move their distal end (interior of the patient) to the operating disposition at the intended internal site of the surgery.

The body, however, contains many surgical sites where the insertion of a probe is constrained. That is to say, that although the probe is conveniently inserted along a constrained path at many surgical sites, it cannot be manipulated proximally to achieve the desired surgical result because the space into which it was inserted is so restrictive it does not otherwise accommodate gross side-to-side motion (or even rotation) of the probe without significant risk of injury to vital structures. In other words, once the surgical probe is in place, it cannot be moved about easily, other than the original "in-and-out" motion by which insertion to the surgical site occurred in the first place. Transecting of the transverse carpal ligament for the relief the carpal tunnel syndrome is an example of such surgery where movement of a probe is severely restricted.

The carpal tunnel syndrome is a well established symptom complex resulting from median nerve compression at the wrist. Referring to FIGS. 1 and 2, the carpal tunnel T is located on the palmar aspect of the wrist (carpus or wrist bones) (see aspect of FIG. 1) between the distal wrist flexion crease 14 and roughly the mid palm. The anatomy of the carpal tunnel in its contents is shown in relation to the surface structures in the section of FIG. 2. The median nerve 20 is superficial on the radial aspect of the flexor tendons 24 and branches, just distal to the distal border of the transverse carpal ligament L. Those familiar with anatomy will know that four superficial flexors, four deep flexors, the flexor pollicis longus and the median nerve normally travel through this tunnel.

Three of four boundaries of the carpal tunnel are essentially inelastic (see bones B in FIG. 2). The dorsal, radial, and ulnar borders form the U-shaped configuration which is open palmarly. The fourth side, the palmar side, consists of the transverse carpal ligament.

Any condition, systemic or local, which reduces the normal available cross-sectional area of the carpal tunnel—either by increasing the volume of contents or by decreasing the diameter of the tunnel—causes local constriction of the median nerve (the structure most sensitive to compression). The most common symptoms are those of sensory abnormalities in the median nerve distribution of the hand. See 20, FIG. 1. These include hyperesthesia (acute irritating hypersensibility), paresthesia (burning, tingling "pins and needles" sensation), hypoesthesia (decreased sensibility) and pain.

Surgery is indicated for cases of carpal tunnel syndrome retracting to conservative care, particularly those with obvious muscle atrophy of the median enervated thenar muscles. The purpose of the surgery is two-fold: (1) to release external pressure on the median nerve and (2) to diagnose and treat the pathology responsible for the nerve compression.

The tarsal tunnel has surgical problems analogous to the carpal tunnel.

As is well known to those specializing in hand surgery, problems exist upon surgery in the wrist. Simply stated, the joint interfaces at the wrist manifest with problems such as tears in the triangular fibrocartilage, chondromalacia, arthritis, irregularity in the articular surface, synovitis, and loose bodies floating in the joint, causing pain.

The elbow is analogous to the wrist, except that the elbow does not have triangular fibrocartilage or the problems associated with it.

Similarly, the ankle has surgical problems comparable to those of the elbow.

The temporomandibular joint has surgical problems similar to those of the wrist, with the additional complication associated with disease states of the articular disc (meniscus), and scar tissue adhesions.

Conventional treatment as performed in other joints (i.e., the knee) is difficult or prohibitive in the wrist, ankle, elbow, and temporomandibular joint because of the severe limitation of space within these joints, making the positioning of multiple visual/therapeutic devices to the injury site impossible without causing iatrogenic injury.

Breast surgery is another procedure where the apparatus and process of this invention is applicable.

Breasts are augmented or made larger by an implant. The implant is a foreign body. All foreign bodies have scar tissue deposited around them. When the scar tissue is deposited and either contracts or shrinks, the breast implant becomes hard. This causes a disfigurement in the breast shape, and if the scar tissue grasps a nerve or if an otherwise hard distended implant impinges upon a nerve, this causes pain.

Conventional treatment includes two procedures. The first is closed capsulotomy where one squeezes the breast and bursts the breast capsule. This is ineffective because the implant can also pop. This procedure can also causes pain to the patient and pain to the surgeon.

The second procedure is the so-called open capsulotomy. In this procedure an incision is made, and the surgeon deflates and removes the implant under direct inspection. Thereafter, surgical entry is made into the evacuated capsule with at least two or three instruments, and the surgeon cuts the capsule, recreating a large pocket. Thereafter, a new implant is inserted. This latter procedure increases cost, prolongs the operation, and increases morbidity, including the potential for bleeding (and scarring).

Laser surgery has been used in other body sites before. Most commonly, and analogously with respect to this invention is laser surgery on various joints within the body, especially on the knee.

Most sites in the body have the advantage of providing proximal manipulation of the operating instrument, especially the knee. That is to say, the surgeon by the manipulation of the device external to the patient, gets the operative end of the device internal of the patient to move to an operating position. Another example of such an instrument is a laparoscope, an instrument utilized in operations on the abdomen and, in particular, the gallbladder.

Typically, the laparoscope is a multichannel instrument carrying a fiber probe for discharging surgical energy in one channel and an optical viewing fiber in another channel. Additionally, it is common with such devices to provide for suction, irrigation, and a tube for the insertion and removal of various tissue grasping devices. There are usually done through separate openings leading to the operation site.

In a laparoscope, the energy discharging fiber at the end of the probe can be moved within the field of view provided by the fiber. The energy discharging fiber is arrayed parallel to the longitudinal axis of the probe. At the tip of the probe, there is defined a fiber end holding section of the probe which raises and lowers with respect to the elongate axis of the probe.

In surgery, the physician first points the entire probe in the direction of or at the surgical site. The surrounding anatomy of the patient is conformable; it permits the probe to be moved relative to the patient until the operative tip is near the surgical site. Thereafter, and when the probe is adjacent to the surgical site, the surgeon raises or lowers the fiber end holding section of the laparoscope to the angle necessary to direct the surgical energy discharged from the tip of the fiber. Thereafter, the entire probe is rotated to direct the energy discharging fiber to the correct angle relative to the axis of the probe for the surgery.

The reader will understand that the above-mentioned surgical techniques for parts of the body where a probe may be manipulated proximally are simply not applicable to restricted operating sites in the body where the probe is constrained, particularly carpal tunnel surgery, tarsal tunnel surgery, surgery of the wrist, ankle or elbow, surgery of the temporomandibular joint, and surgery on breast capsules after augmentation. Moreover, in the case of breast implants, actual surgery between the interface of the implant scar tissue capsule and the implant must occur without damage to either the implant or the anatomy adjacent the capsule.

SUMMARY OF THE INVENTION

An apparatus and concomitant process for surgery utilizing a probe for the discharge of incising, transecting or tissue treatment energy is disclosed, the probe being adaptable for the surgical process when the constraints of the anatomy through which the probe is inserted substantially inhibit or prevent proximal manipulation of the probe. The disclosed instrument and related process is particularly useful in a process for surgery on the transverse carpal ligament of the hand, tarsal tunnel surgery, surgery in the wrist, ankle, or elbow, surgery in the temporomandibular joint, or breast capsule surgery with breast implants in place.

The probe defines at least one interior rigid or semirigid conduit having an opening, this opening being preferably at the distal end of the probe. The probe is either rigid or semirigid. For example, in the case of carpal tunnel surgery, the probe is given sufficient length for insertion into the hand with said opening disposed within the carpal tunnel to provide access to the hand.

The interior conduit of the probe includes an optical viewing device. This optical viewing device protrudes from the opening of the probe for view at the end of said probe. Optimally, the viewing device is stationary with respect to the probe; optionally, the viewing device can be provided with remote motion with respect to the probe.

The probe is provided with at least one conduit for conducting energy sufficient for the transection, incision, or treatment of the surgical site of the body where probe insertion occurs and terminates in the field of view of the viewing device. This is required so that the conduit may be observed at the interface of energy application during the discharge of energy.

There is required means for the distal manipulation of the conduit releasing the transecting, incising or treatment energy at the end of the probe without concomitant proximal manipulation of the probe, other than along the original "in-and-out" and rotational path through which surgery occurred.

According to the process of this invention, when the probe is inserted at the surgical site, the surgical site is such that side-to-side motion of the probe relative to the path of insertion of the probe is prohibited—other than the original path of insertion and any motion of rotation along the axis of the probe. Once such entry has been accomplished, the surgical site is visualized. For example, where the surgical site is the carpal tunnel in the wrist, the transverse carpal ligament is sighted through said optical viewing device at the opening in said probe from the carpal tunnel to and toward the palmar side of the hand. As a further example, where the capsule of a breast implant requires surgery, the scar tissue capsule is visualized at portions of the capsule where incisions are to be made.

Without proximal side-to-side manipulation, and during the visualization, energy for transecting, incising or treating the surgical site is introduced. The introduction and local direction of the energy occurs once the probe is inserted; without the proximal manipulation of the probe side-to-side only motion in the "in-and-out" or rotation mode is provided from the proximal end of the device mode. As will be apparent in the "pistol grip" embodiment shown, rotation of the probe with respect to the pistol grip is contemplated.

A deployable shield is provided on the probe. This deployable shield is moveable from a contracted disposition relative to the probe to an expanded disposition relative to the probe. Preferably, one extremity of the deployable shield is rigidly attached to the probe. Another extremity of the deployable shield is affixed to an actuating member on the probe. When the probe is inserted, the shield is collapsed. When the probe is at the surgical site, the shield is expanded.

The deployable shield has two functions. First, the shield prevents portions of the anatomy at the surgical site which are not intended for surgery to be restricted away from the surgical site. Secondly, the shield effectively prevents the discharged energy from affecting healthy nearby tissue which is not intended to be transected, incised or treated.

In one embodiment of this invention, there is provided a protective flexible mesh structure disposed about the exterior of said probe. This protective flexible mesh structure includes semirigid woven struts forming the side walls of the collapsible flexible mesh structure. The flexible mesh structure is attached at one end of the probe, preferably at the distal end. The flexible mesh structure is attached at the opposite end to a reciprocating member moving along the probe, preferably at an exterior sleeve.

In operation, the reciprocating member, preferably a sleeve, is collapsed onto the probe during the insertion of the probe. Once the instrument has reached the surgical site, the flexible mesh structure is expanded about the probe prior to the supplying of energy to the surgical site.

In an alternate embodiment, a balloon is disposed about the exterior of the probe. This balloon is collapsed to the probe during insertion of the probe. Once the probe reaches the surgical site, the balloon is expanded. In the expanded disposition, the balloon physically screens out anatomy from the surgical site.

It will be understood that the side walls of the balloon are capable of being opaque to the energy discharged at the surgical site. Moreover, and because of the physical separation from the surgical site, shielding of other portions of the anatomy occurs from full effect of the radiation occurs.

The disclosed instrument and shield are especially designed for deployment in extremely restricted anatomical volumes. Such volumes are found in the carpal tunnel, the joints of the wrist, ankle and elbow, the tarsal tunnel, the temporomandibular joint, or at the interface of a breast capsule and breast implant. It will be understood that once the shield is deployed, manipulation of the probe is further restricted; in short, the expanded volume of the shield attached to the probe further limits the ability to proximally maneuver the probe so that the energy discharging portion of the probe will not damage tissue beyond the surgical site.

Because of this disability, it is required that the conduit for the discharge of the energy be completely maneuverable at the distal end of the probe without concomitant proximal manipulation. Accordingly, two embodiments are provided.

In a first embodiment, the energy discharge conduit is encased within a second conduit which itself can be directed with respect to the probe. According to this embodiment, the energy discharging conduit includes a semirigid conduit having stiff tensile members in the side walls of the semirigid conduit. Preferably, at least two such members are utilized so that the energy discharging conduit can move up and down and side to side with respect to the probe.

In a second embodiment, the conduit from which the energy is discharged is threaded interior to the conduit on which the shield is disposed. This interior conduit has a member which can dispose the energy discharging conduit at an adjustable angle with respect to the end of the probe. By the expedient of moving the energy fiber to the requisite angle with respect to the axis of the probe, and rotating the interior conduit with respect to the exterior conduit, complete positioning of the conduit discharging the energy to the surgical site can occur.

The reader will understand that the disclosed concentric conduits have additional utility. For example, they can be utilized for either ventilation, irrigation, and suction to or from the site of the surgery.

It will be understood that the functions of suction and irrigation are not to be casually treated in this disclosure. It will be understood that the because the surgical probe herein disclosed is confined to such a tight volume or surgical interface, suction at a minimum is required to preserve vision of the transection, incision or treatment. Further, the suction is disposed with respect to the probe in such a disposition that the suction of fluids is away from the line of sight between the optical viewing device and the interface of surgery.

BRIEF DESCRIPTION OF THE DRAWINGS

Other objects, features and advantages of this invention will become more apparent after referring to the following specification and drawings in which:

FIGS. 4A and 4B are respective side elevation and plan views of the disclosed probe with connection here being shown in FIG. 4A to remote viewing, lasing, and suction devices;

FIGS. 5A, 5B and 5C are respective perspective, side elevation and plan views of the tip of the probe illustrating the relationship of the suction device distally from the end of the probe for the withdrawal of smoke and soot from the surgical site and away from the view of the fiber-optic device and the surgical procedure at the energy discharging conduit;

FIGS. 11A, 11B and 11C are respective sections of the wrist, palmar side of the hand, and back side of the hand;

FIGS. 12A and 12B are respective illustrations of the anterior and posterior portions of a human foot;

DESCRIPTION OF THE PREFERRED EMBODIMENT

Figure 3:
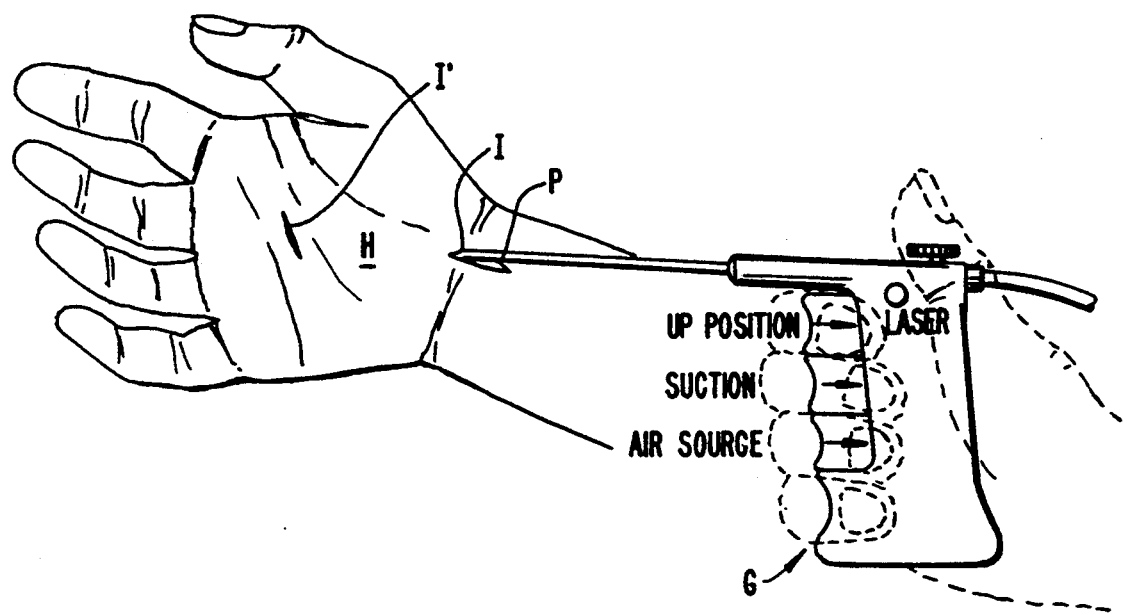
FIG. 3 is a perspective view of the probe of this invention attached to a pistol grip.

Referring to FIG. 3, a pistol grip G having a protruding probe P is illustrated. The probe P is being placed within a longitudinal incision within hand H. Insertion occurs through a longitudinal incision I at the distal volar of the forearm at the base of hand H. An alternate incision for insertion of the probe is shown at I'.

The gross manipulation of the disclosed surgical instrument having been described, its operative portions can be set forth.

Referring to FIG. 4A, a pistol grip G is illustrated with probe P protruding from the "gun barrel" position relative to the grip. It will be understood that since the subject of this invention relates to surgery in small and confined places, the probe is made as small as practical. Further, the probe—and all its contents—are can be semirigid. That is to say, the stiffness of the probe is sufficient to permit insertion; but flexible enough to accommodate blunt dissection at the tip of the probe so that the probe P finds its way between anatomy structures without incising them. This being the case, the reader will understand that the drawings illustrating the best mode of this invention contemplated at this time are not necessarily to scale; such dimension may be added by the routineer.

A minimum of two conduits are required for probe P. The first conduit is for an optical viewing device O. Optical viewing device O can have any standard configuration. Preferably it comprises an optical fiber 14 having a wide-angle lens 16 at the end. The optical fiber is connected to a viewing device 20, which viewing device can either be an eyepiece or a monitor for displaying the field of view seen at lens 16. I contemplate other viewing devices including remote and miniature video cameras.

Secondly, the probe must include a conduit 38 for transmitting energy sufficient for transection of the transverse carpal ligament. Conduit 30 terminates at end 34 where the energy within the conduit is discharged from tip 36 at the surgical site. This discharge must occur within the field of view of the lens 16 so that transection occurs within the view of the surgeon.

In the embodiment here shown, an optical fiber 38 connects to a laser power source including a laser amplifier. The optical fiber is capable of in-and-out motion with respect to conduit 30; thus the fiber as shown is maneuverable with respect to the probe P. For example, I have constructed the probe from a hypodermic needle having a bent end; an optical fiber was moved with an "in-and-out" motion with respect to the hypodermic needle. An optical fiber viewing device was taped to the needle. The device was sufficient for surgery related to the transection of the transverse carpal ligament.

It will be found convenient to rotate probe P with respect to grip G. Such rotation is schematically shown at arrow 66.

Referring to FIG. 5A, I illustrated the probe P at the blunt dissector end 61 of the probe. It will be seen that the opening 62 of the probe P defines a suction entrance volume 62, this volume having multiple purposes. First, and most apparently, it draws the smoke and soot of surgery away from the view between lens 16 and tip 36. Secondly, and as the probe advances, it defines an upwardly exposed cavity in which the disclosed surgery can occur. Finally, and at pad 63, a relative hard spot is defined at the tip of the probe P whereby structure can be impressed (felt) with the probe P.

I contemplate construction of the probe from molded, semirigid construction materials such as those selected from plastics commonly used in surgery. Naturally, other materials will suffice.

Referring to FIGS. 5B and 5C, I disclose a conduit 34 having an energy fiber which is maneuverable with respect to the end of probe P. Specifically, the motion here illustrated is side-to-side and up-and-down motion. Such motion is well known. By way of example, endoscopes commonly accommodate such motion at their tips. An example of such an endoscope is Nasal Endoscope manufactured by the Makatsu Corporation of Tokyo, Japan. While this endoscope is larger than the fiber steering conduit I contemplate, this is a matter of scale.

Figure 6:
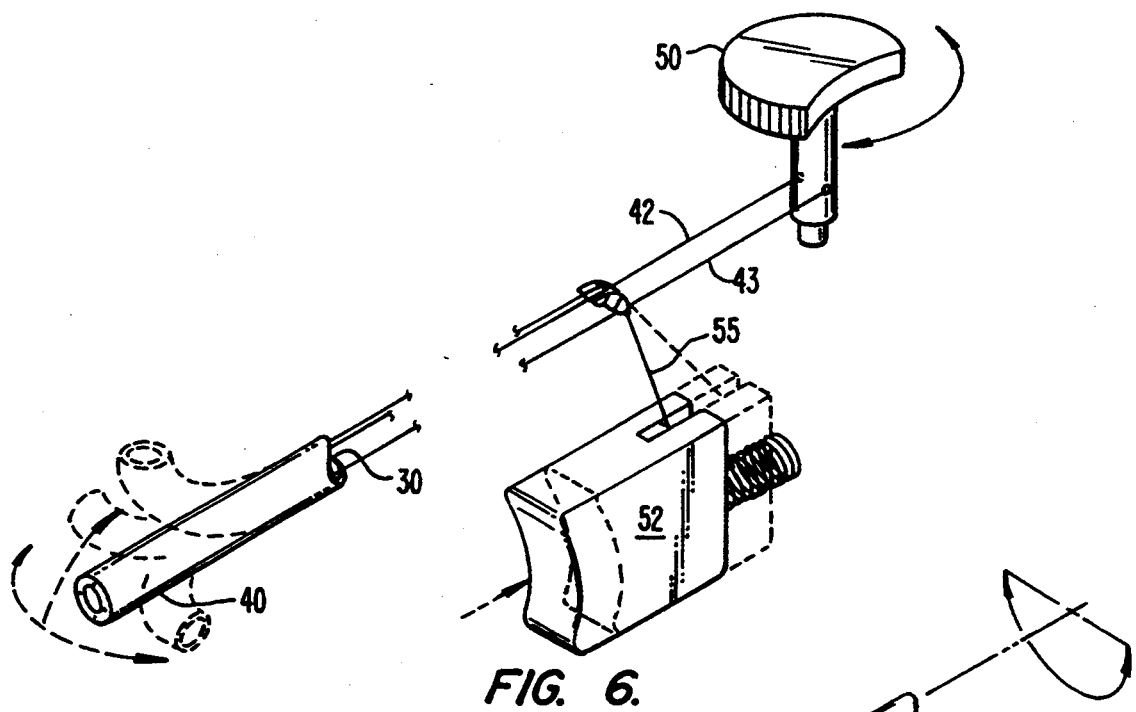
FIG. 6 is a perspective illustration of the operative energy discharging fiber encased within a directionally steerable outer sheath such as that found on endoscopes, with the control structure to the tip of the directionally steerable structure being schematically shown.

Referring to FIG. 6, the operation of steering function can be understood. Specifically, a semirigid end 40 is provided around conduit 30. Tensile elements 42, 43 are provided along the side walls of the semirigid end 40. As is well known, by providing differential tension on elements 42, 43, remote steering of probe P at the distal end can occur. I prefer to place wires 42, 43 to a knurled wheel 50 for the side-to-side direction of the optical fiber. Up-and-down motion can be directed by wire 55 connected in a similar manner to trigger 52 on grip G (not shown in FIG. 6.

The reader will appreciate it may be desirable to move the optical viewing device independent to the probe and energy fiber at tip 36, construction will duplicate the structure shown for moving fiber 34 at tip 36.

In the preferred embodiment illustrated in FIG. 4A, I include a suction conduit 60 with an end 61. As can be seen in the side elevation of FIG. 4A, end 61 is distal to both the end of the fiber 36 and lens 16. Suction conduit 71 is connected to suction pump 64.

FIGS. 5B and 5C show respective side/plan elevations of the suction only. It can be seen that opening 62 and end 61 of suction conduit 60 is disposed immediately underneath end 36 of fiber 34. In this disposition, and during the surgery, smoke and soot that might obstruct the view of end 36 of fiber 34 are removed. The field of view from lens 16 is schematically shown.

Figure 7:
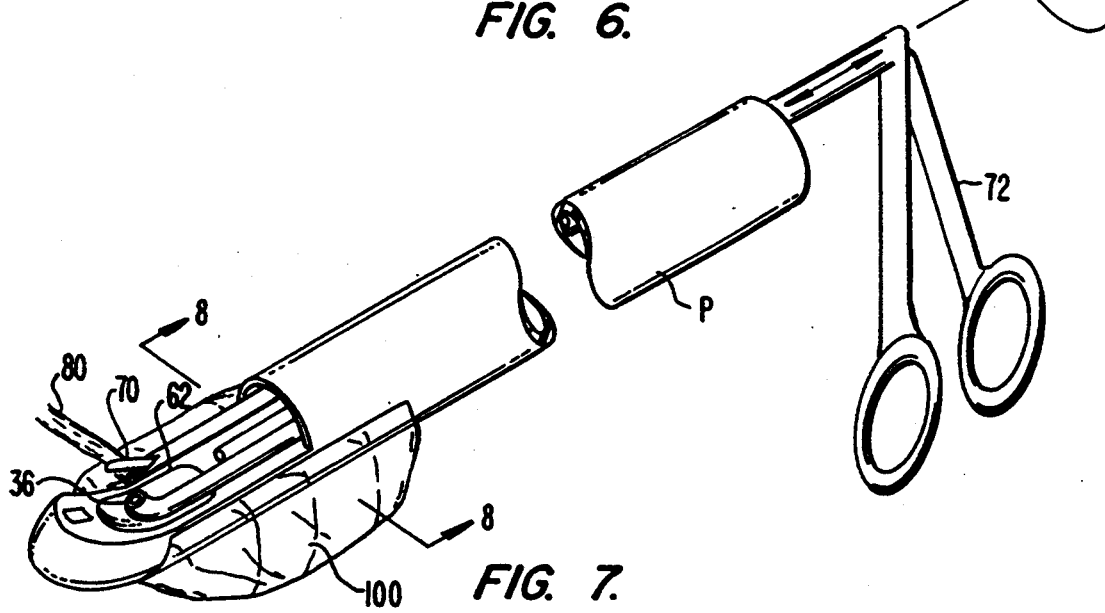
FIG. 7 is a perspective view of the semirigid probe illustrating the insertion of a grasping and manipulating surgical appliance in the combination of the disclosed probe, the schematic format here shown omitting the pistol type handle for ease of understanding, this illustration setting forth in perspective view a deployable shield in the form of an expansible balloon.
Figure 8:
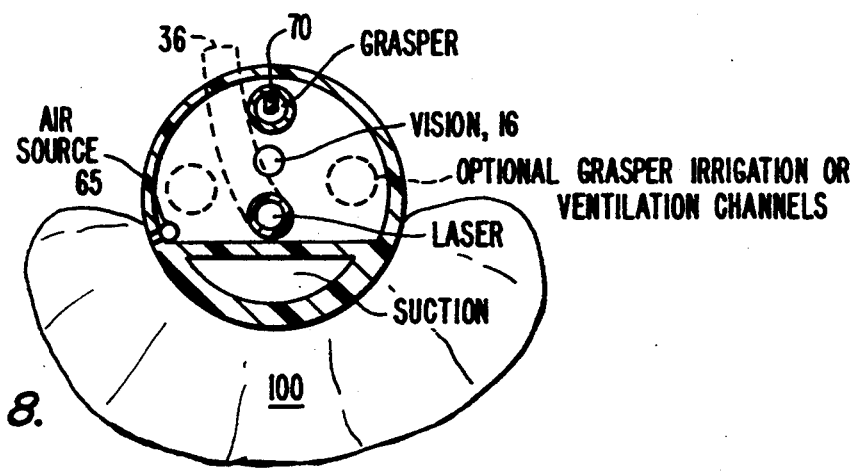
FIG. 8 is a side elevation section at the end of the probe along lines 8—8 of FIG. 7 illustrating the relative elevations of the appliance members and illustrating the balloon as an inflated structure for performing the surgery disclosed.

Referring to FIG. 7, I illustrate two additional features of my invention. First, I illustrate grasping devices utilized in combination with probe P. The surgical grasping device contemplated is manufactured by the Acuflex Corporation of Mansfield, Mass. This device includes blunted, opposed jaws 70 at the tip with a scissors like handle 72, which scissors like handle 72 can be rotated remotely from the instrument. I choose not to illustrate the pistol grip G for ease of understanding. In the current embodiment, limited towards and away motion is provided by handle 72 as well as rotation.

It will be seen that in the schematic of FIG. 7, I illustrate a tissue member 80 being grasped, with tip 36 having just severed its outer portion with disposal to underlying suction entrance 62. Severing on either side of grasping device 70 is contemplated.

FIGS. 7, 8, 9A and 9B illustrate my instrument with an additional attachment.

Figure 9A:
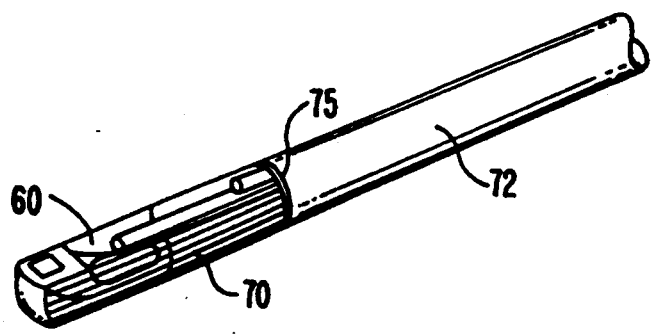
FIG. 9A is a perspective view of an alternate embodiment of the probe including a collapsible flexible mesh structure, the flexible mesh structure here being shown in the collapsed position on the exterior of the probe for insertion of the probe to the surgical site at the transverse carpal ligament.
Figure 9B:
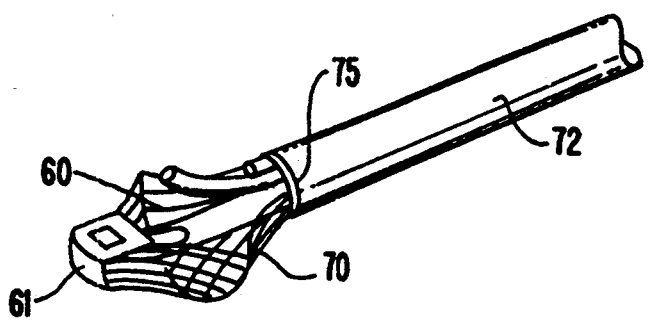
FIG. 9B is a perspective view of the alternate embodiment of the probe showing the collapsible flexible mesh structure expanded as it would be in the surgical site underneath the transverse carpal ligament for shielding tissue, such as nerves and tendons, from the site of the transection of the transverse carpal ligament; and, FIGS. 10A and 10B are illustrations of a protective sheath adjacent the energy discharging conduit for preventing sticking of the fiber of tissue and providing a self cleaning action.

Referring to FIGS. 9A and 9B, the exterior of the probe P is covered with a flexible mesh structure 70 attached to the tip of probe P. Flexible mesh structure 70 in the collapsed position illustrated in FIGS. 9A. Flexible mesh structure is attached at 75 to a sleeve 72 on probe P. Other reciprocating members sliding along the distal end of probe P may also be used. Attachment to end 61 of probe P occurs as well.

To maintain the flexible mesh structure 70 in the closed position, sleeve 73 biases flexible mesh structure 70 away from the end of probe P. (See FIG. 9B).

Referring to FIG. 9B, opening of flexible mesh structure 70 on the end of probe P can be understood. Sleeve 73 is moved forwardly. Flexible mesh structure 70 expands away from the sides of probe P while remaining attached to the distal end of probe P.

It is important to observe that flexible mesh structure 70 only covers the bottom of the probe P below suction conduit 60 at end 61. That is to say, with respect to the longitudinal axis of probe P illustrated, only that portion of the probe P disposed away from the transverse carpal ligament is shielded, the shielding occurring for approximately 180° around the axis of probe P.

Figure 1:
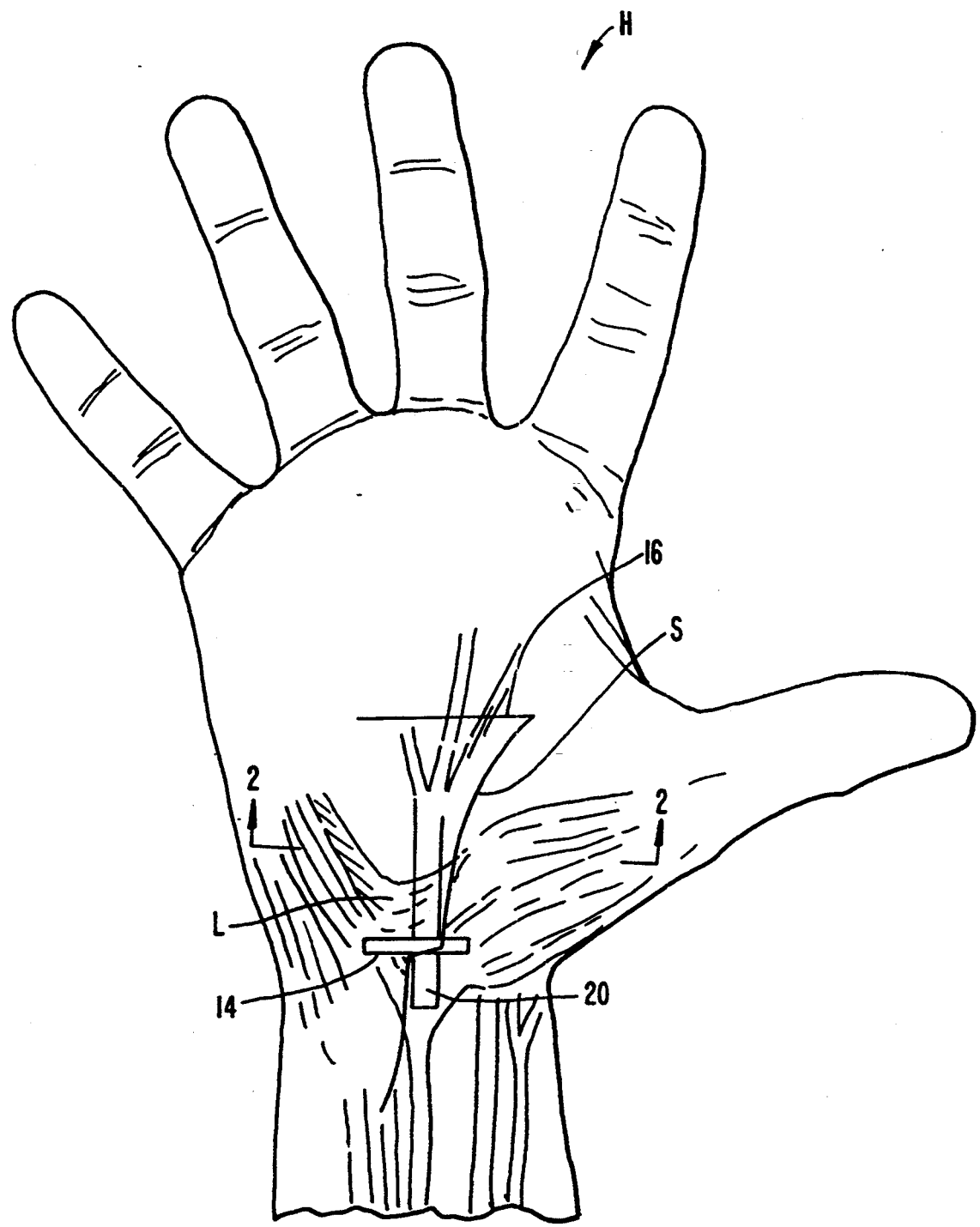
FIG. 1 is a palmar view of the a right hand with surgically important structures noted on the exterior of the hand.
Figure 2:
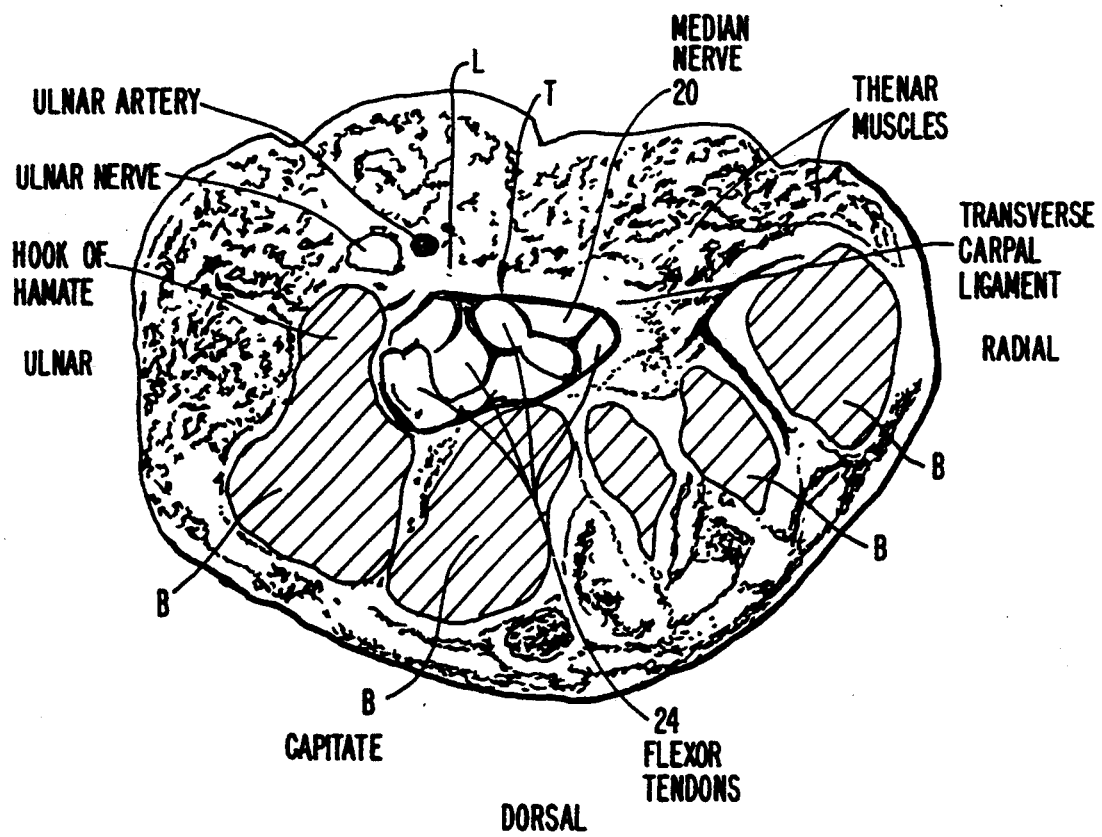
FIG. 2 is a cross section of the wrist at the level of the hook of the hamate illustrating the anatomy of the carpal tunnel and its contents.

The function of the flexible mesh structure 70 is easy to understand. Specifically, tendons and nerves (See FIG. 2) within the carpal tunnel are shielded and kept away from the transection surgical site.

Referring back to FIG. 8, it will be understood that the deployable shield that I contemplate can be a balloon 100. Typically, balloon 100 is fastened to the sides of the probe P, just below suction entrance 62. It extends around the bottom circumference of the probe—it does not extend over suction entrance 62. Inflation and deflation occurs through conduit 65. In this disposition, preferred protection in the format of a deployable shield is provided.

Figure 10A:
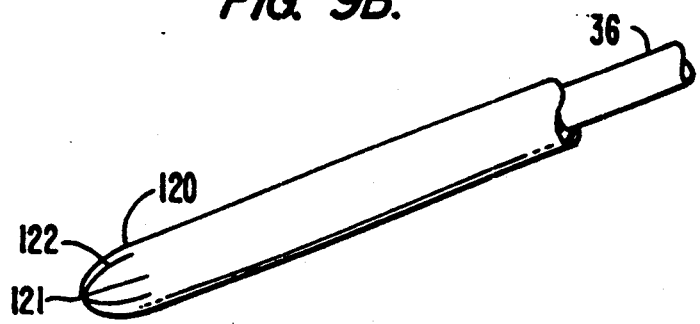
Figure 10B:
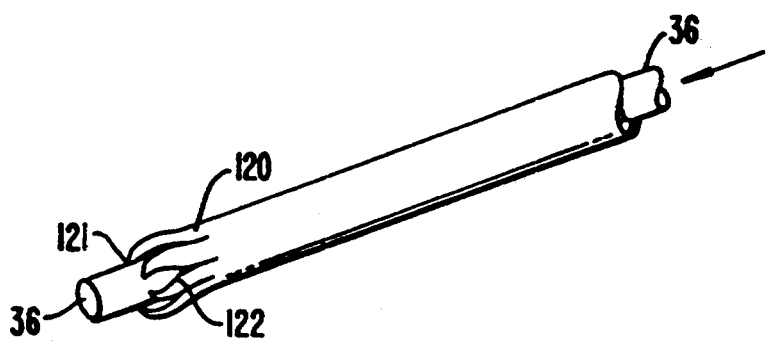

Referring to FIGS. 10A and 10B, I contemplate a self-cleaning and protective sheath 120 over fiber end 34 covering tip 36. Simply stated, controlled in-and-out motion (pistoning) is contemplated. Since tip 36 is in effect active, tissue will adhere. Further, upon advance of the probe P, tip 36 could become impaled. This being the case I contemplate a cover 120 having spherical end 121 with serration 122. When the tip 36 is retracted, cleaning of the fiber end occurs. In the retracted position, advancement with reduced risk of impalement can occur. For use, fiber 34 is advanced out of sheath 122 opening spherical end 121 at serration 122.

Presuming the skill and knowledge of a hand surgeon, the operation is easy to understand.

In the disclosed operation process, anesthesia is provided and a longitudinal incision I is made at the distal polar of the forearm (or wrist). Optimally, a solid probe having the overall dimension and cross section of probe P is inserted to create a temporary tunnel for the probe of the instrument. This typically occurs with a transitory compression of the median nerve 20 (See FIG. 2).

The probe P of the instrument is then inserted underneath the transverse carpal ligament T, and the ligament visualized for its entire span. The suction pump 64 is turned on and transection commenced by the discharge of energy from the optical fiber 34 at end 36. Appropriate in-and-out, side-to-side, and up-and-down movement of the fiber 34 at end 36 in conducted under the view of the surgeon through lens 16. During the discharge of the transecting energy, conduit 60 with the suction draws the smoke and soot of the laser surgery out of the field of view of the orthoscope. Surgical shield 70 is preferably deployed. When the transverse carpal ligament is transected, the probe is withdrawn, the longitudinal incision sutured closed and the hand placed in a post surgical splint for recovery.

FIGS. 11A and 11b illustrate the wrist joint and these are the portals of entry and there are six reference portals which you can insert my probe for the purpose of entering the joint and treating problems within, inside the wrist.

In the cross-section the portals are labelled between the six extensor compartments in the back of the hand, named with 201–205 going from the radial side, which is the thumb side, to the ulnar side, which is the little finger side. So, between the first and second extensor compartment are portals 201, between the third and fourth extensor compartment there is a portal 202, between the fourth and fifth extensor there is a portal 203, and on either side of the sixth extensor compartment is a portal 204, 205, the portal being a zone of entry. That is with the joint between the forearm bones and the wrist bones.

Now with respect to each one of those portals at the wrist, they basically meets my qualification if the surgical site is a joint and a probe is inserted to it, the probe, in reaching the surgical joint, is going to be constrained. Proximal manipulation of the probe in order to effect the movement of the distal end of the probe P for surgery is impracticable. Rather, it is going to be the movement at the distal end of the probe P that is going to do the surgery.

Referring to FIG. 11C, the same thing holds true for the other wrist joint, which is the midcarpal wrist joint, which is illustrated with respect to the back side of a hand. Two surgical portals 208, 209 for the midcarpal joint. These particular portals are between the proximal and midcarpal bones interspaced between the extensor tendons as shown.

Figure 16:
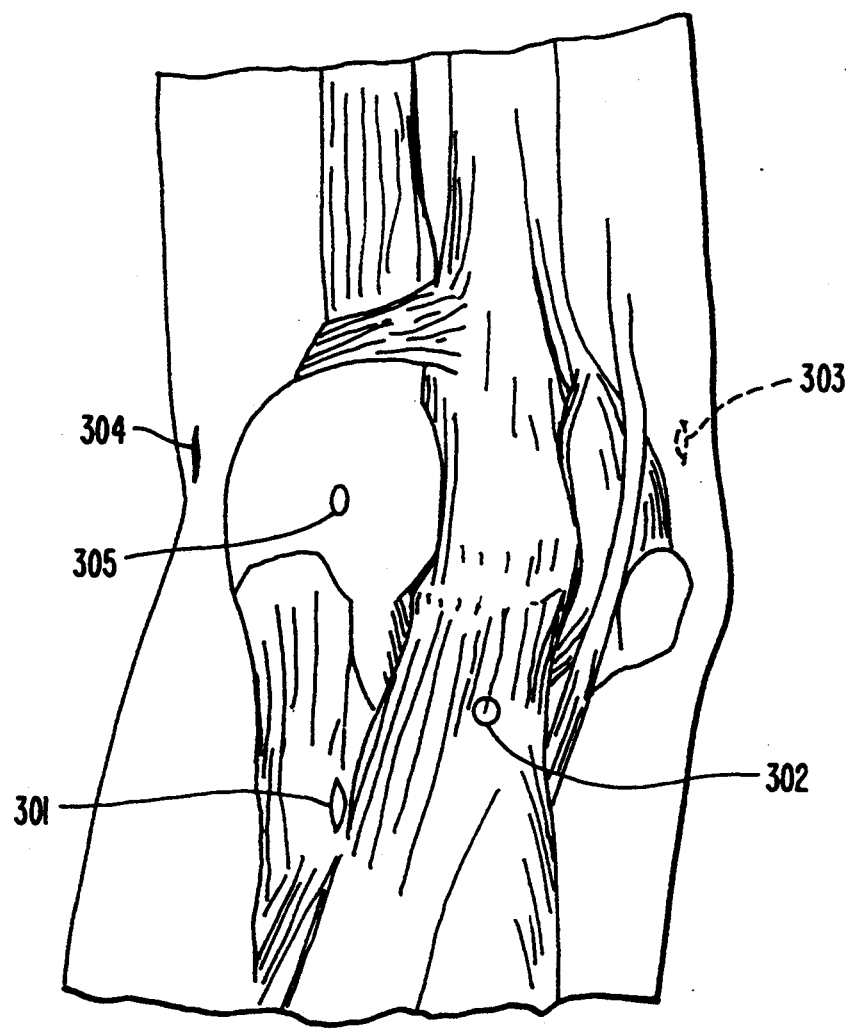
FIG. 16 is a schematic of the human elbow.

Referring to FIG. 16, the structure of the elbow is illustrated. The posterolateral portal 301, the straight posterior portal 302, the anteromedial portal 303, the anterolateral portal 304, and the straight lateral portal 305 are schematically shown. These portals, and the surgical sites underlying them, generally meet the qualifications that proximal movement of the probes to accomplish distal movement of the energy discharging fiber is not practical because of either the constraint of the surrounding tissue or possible damage to the surrounding anatomy.

And the reason that there are so many portals in the wrist, unlike the knee, is again because the knee permits proximal manipulation of the device to get to your operative site, whereas in the wrist you cannot really manipulate this proximally to get to all fields. That is why it is required to specify so many different, separate portals in this area of the human anatomy.

Regarding the portals of entry to the foot at the ankle, these again have the same problem. Referring to FIG.

12A, from the anterior aspect of the foot, which is the opposite side of that which is walked on, is illustrated coming toward the viewer. You walk on the plantar surface and the side that you put the scope in is either in the anterior (FIG. 12A or the posterior part (FIG. 12B), which is by the Achilles tendon. So, there are three anterior portals 210, 211, 213, and three posterior portals 214,215, 216, being anterior lateral, anterior central, anterior medial; posterior being posterior lateral, trans-Achilles (which means you go right through the Achilles tendon) and the posterior medial portal. Again, the problem here is that, the reason we have so many portals is because of the limited space in that joint, unlike the knee, which means you cannot manipulate the instrument proximally in order to get the distal end of the probe to move for operative engagement within the surgical site. As I disclose with my preferred probe, all movement has to be in the operative site at the distal end of the probe without concomitant movement of the proximal side.

Figure 13:
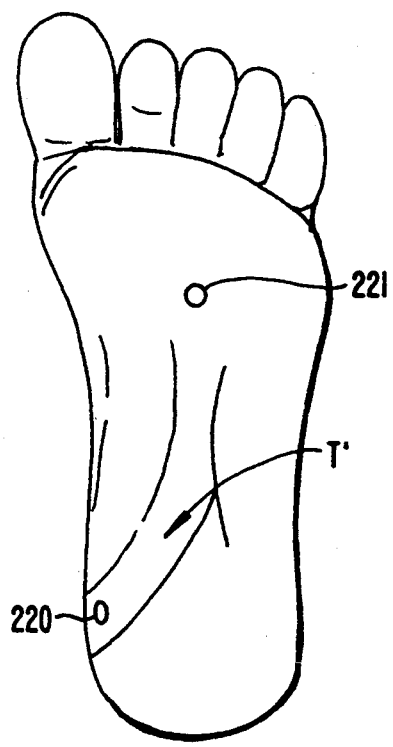
FIG. 13 is an illustration of the planar side of the foot to show the tarsal tunnel.

Referring to FIG. 13, the plantar side of the foot to demonstrate surgical ports of entry having the same constraints. It is to be noted that like in the hand where there is a carpal tunnel, in the foot there is tarsal tunnel T'. The tarsal tunnel is like the hand in the sense that there are tendons, nerves, and blood vessels going through a space, which has a fixed boundary on three sides, except for the fourth boundary, which is a ligament. That ligament basically is the soft structure. Anything that causes increase in content volume in that space will cause pressure on the structures within that space and the structure most sensitive to pressure is the nerve causing symptoms. Again, the disclosure herein sets forth a surgical probe instrument that is ideal for that because it permits transection of that tunnel without a fairly large incision on the bottom of the foot, which would take a long time to heal.

Entry occurs on either the plantar surface of the foot 221, or preferably the instep 220.

Figure 14:
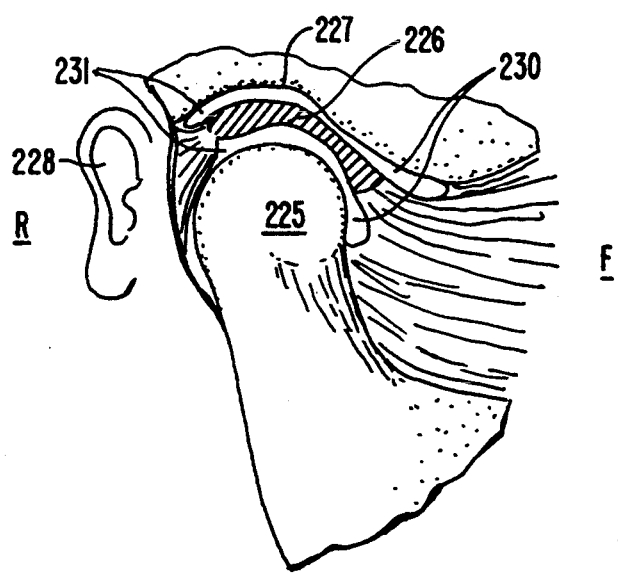
FIG. 14 is a section in the skull adjacent the mandibular joint.

Referring to FIG. 14, the temporomandibular joint is illustrated. That is the joint in the jaw where the mandible meets the cranium or the skull. The condyle 225 of the mandible; the articular disk 226; the cranial base 227; the ear canal 228; the front F of the person; the back R of the person. The points of entry are directly in front of the ear canal 231 or in front of the condyle. Potentially, there are four entry points.

Figure 15A:
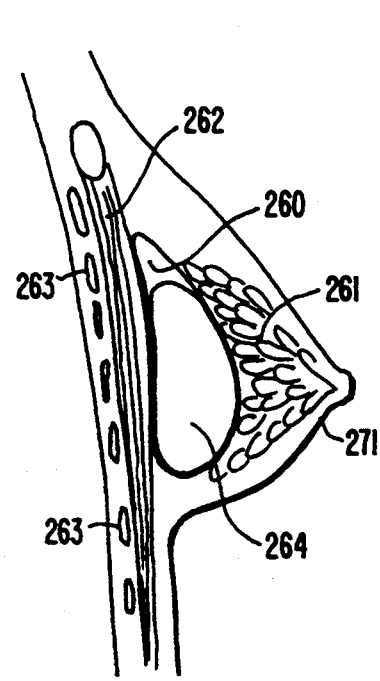
FIGS. 15A–15B are representative illustrations of two positions of female breast augmentation implants with FIG. 15C being a schematic of a procedure preferably utilizing the semirigid probe of my invention.
Figure 15B:
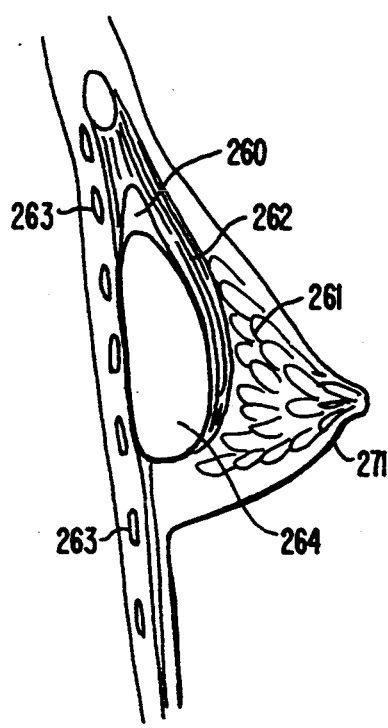
Figure 15C:
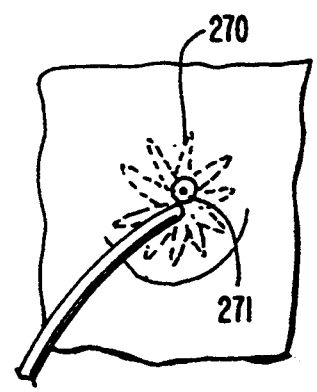

Referring to FIG. 15A, 15B and 15C, a female breast is illustrated having an implant 264. The breast implant 264 is shown in 15A and 15B following breast augmentation. The implant is shown in FIG. 15A above the pectoralis muscle or below the pectoralis muscle. In either case, a capsule or scar tissue 260 forms around the implant 264.

In FIGS. 15A and 15B, implant 264 is shown within a scar tissue capsule surrounding the implant 264. Breast tissue 261, the pectoralis muscle 262, and the anterior rib cage 262 are also shown.

As is well known, the scar tissue of the capsule can either contract or shrink. The breast implant becomes hard. Nerves can either be directly affected by the scar tissue or alternatively the implant itself can pinch a nerve.

The way this problem is treated with the probe is by incising this capsule in a star pattern or cartwheel pattern, see FIG. 15C at 270, dividing the scar, allowing the implant to roam in a bigger pocket, The implant becomes softer again.

The probe P of this disclosure would enter either through the side (not shown) or through the areolar area just to get to the implant at the interface between the implant and the capsule. In such penetration, access to the scar tissue is desired; injury to the implant is to be avoided.

It will be appreciated that in such a procedure, my probe P will be particularly useful if it is of semirigid construction.

It will be understood that surgery by knife is excluded from the contents of this disclosure. Further, It is preferred to utilize laser energy. Laser energy ranges sufficient for the performance of the surgery set forth in this invention for the transection of the transverse carpal ligament are contained in U.S. patent application Ser. No. 07/621,451 of Peter S. Hertzmann and Jordan K. Davis filed Nov. 30, 1990 and entitled A METHOD FOR PERFORMING PERCUTANEOUS DISKECTOMY USING A LASER, issued as U.S. Pat. No. 5,201,209. This application is a Continuation-In-Part of U.S. patent Ser. No. 07/463,759 filed Jan. 12, 1990. This application and especially its laser frequency ranges are incorporated to this disclosure by reference.

It will be apparent, that the disclosed operating probe will be applicable to other operating sites in the body. In an application filed of even date herewith, It is specified by location operation sites. These operating sites are all adjacent to constrained cavities having narrow substantially nonmanipulable entrance confines. These narrow substantially nonmanipulable entrance confines inhibit, retard and practically prevent appreciable side-to-side motion of a probe. That is to say, the probe can not be manipulated at its controlling end other than accommodating in, out and rotation. The whole surgical movement of the system has to occur at the distal end—and not by side-to-side motion of the probe at the controlling end.

It will be understood that this specification is exemplary and the invention herein to be liberally construed within the scope of the attached claims.

What is claimed is:

1. A probe apparatus for surgery in an operating site having narrow substantially non manipulable entrance confines inhibiting side-to-side motion of said probe comprising:

a probe having a closed blunt non dissecting tip and defining at least one interior conduit having an opening at a distal end, said blunt dissection tip including means for creating a space between tissues in the body of sufficient dimension to facilitate the surgery without interference from collapse of the tissues about the probe;

a suction entrance defined in said space, said suction entrance defined behind said blunt dissection tip of said probe about said space for operation at said distal end of said probe;

an optical viewing device within said probe, said optical viewing device providing visualization of said space for overlying said suction entrance for view at said end of the probe;

means for viewing from said optical viewing device disposed to said end of said probe; and means for grasping disposed to said end of said probe for grasping tissue or structures at said operating site within the view of said optical viewing device whereby said probe may remotely manipulate said grasped tissue or structures at said operating site.

2. The invention of claim 1 and further including:

a non penetrating conduit for energy discharge for transection, incision or treatment at said operating site, said conduit protruding above the suction entrance at said end of said probe and terminating in said field of view of said optical viewing device for the discharge of said energy;

means for supplying energy to said non penetrating conduit for energy discharge for transection, incision or treatment at said operating site;

means for manipulating said non penetrating conduit for energy discharge for transection, incision or treatment with respect to said end of said probe overlying said suction entrance in the view of said optical device at said operating site.

3. The invention of claim 1 and wherein:
said means for grasping is rotatable.

4. A process for surgery utilizing a probe, said probe being a multichannel probe of sufficient rigidity to be insertable in a narrow entrance of an operating site, and without side-to-side and up and down manipulation accommodate blunt dissection of anatomical structures without incising them, said probe having an operating portion for insertion to a position within a patient and a proximal controlling portion for insertion and withdrawal of said probe from a position exterior of said patient, said operating portion having a closed blunt non dissecting tip and a cavity axially displaced behind said tip and shielded thereby for location to said operating site, said probe further having a vision device disposed at said cavity, said vision device having a field of view at said cavity when said probe is within said patient and including a conduit to the proximal manipulation portion for transmitting a view from said cavity of said non dissecting tip to said position exterior of said patient, said probe having a non penetrating conduit for energy discharge for transection, incision or treatment from the proximal controlling portion of said probe exterior of said patient to said operating site of said non dissecting tip within said patient, and said probe having means disposed at a distal end of said non dissecting tip for controlling a relative direction of the energy discharging conduit relative to an operating space of said tip within the field of view of said viewing device, said means enabling change of relative direction of said energy discharging conduit with respect to said operating space behind said non dissecting tip, said process including a series of steps comprising:

inserting said probe to said operating site thus creating a space between tissues in the body of sufficient dimension to facilitate the surgery without interference from collapse of the tissues about said probe, said axial insertion continuing until said cavity behind said non dissecting tip is at said operating site;

visualizing said operating site with said optical viewing device;

supplying said non penetrating conduit with energy discharge for transection, incision or treatment to said operating site during said visualization step; and manipulating said non penetrating conduit through said means for manipulating said energy discharging conduit in treatment at said operating site without concomitant proximal side-to-side manipulation of said probe at said proximal controlling portion of said probe.

5. The process of claim 4 and wherein said insertion step occurs to said operating site within said narrow substantially non manipulable entrance confines inhibiting side-to-side motion of said probe, selected from the class of operating sites including:

carpal tunnel, tarsal tunnel, wrist joint, elbow joint, ankle joint, temporomandibular joint, or shoulders, between natural anatomic tissue planes or scar tissue capsules forming around implants of the breast.

6. The process of claim 4 and wherein said non penetrating conduit for energy discharge for transection, incision or treatment includes:
providing an optical fiber; and,
said supplying step includes:
supplying said optical fiber with lasing energy.

7. The process of claim 4 and wherein said inserting step into the operating site adjacent said constrained space includes:
irrigating and/or ventilating said operating site.

8. The process of claim 4 and wherein said inserting step into the operating site adjacent said constrained operating space includes inserting said probe into the female breast of the human anatomy between the interface of a breast implant and a scar tissue capsule around said breast implant.

9. A probe apparatus for surgery in an operating site having narrow substantially non manipulable entrance confines inhibiting side-to-side motion of said probe comprising:

a probe defining at least one interior conduit having an opening at a distal end, said distal end being insertable into said entrance;

a closed blunt non dissecting tip attached to an end of said probe including means for creating a space between tissues in the body of sufficient dimension to facilitate the surgery without interference from collapse of the tissues about said probe;

an optical viewing device within said probe, said optical viewing device providing visualization of said space for providing a field of view of said space;

a non penetrating conduit for energy discharge for transection, incision or treatment at said operating site, said conduit working within said space at said end of said probe behind said closed blunt non-dissecting tip and terminating in said field of view of said optical viewing device for the discharge of said energy;

means for supplying energy to said non penetrating conduit for energy discharge for transection, incision or treatment at said operating site; and means for viewing disposed to said end of said probe during the discharge of energy from said conduit;

said means for defining a space including an expansible and contractible shield mounted to said blunt non dissecting tip of said probe, said shield being movable between a collapsed disposition conformed along a side of said probe to an expanded disposition with respect to said side of said probe whereby said shield may be collapsed with respect to said probe during insertion and expanded when said shield is at said operating site to define said space behind said blunt non-dissecting tip; and means for expanding and contracting said shield attached to said probe.

10. The apparatus of claim 9 and wherein said shield comprises:
a flexible mesh structure disposed about the exterior of said probe;

means for attaching a first portion of said flexible mesh structure at a first location on said probe;

means for attaching a second portion of said flexible mesh structure to a reciprocating portion of said probe whereby upon relative movement between said reciprocating portion of said probe and said first location on said probe said flexible mesh structure expands and contracts about said probe.

11. The apparatus of claim 9 and wherein said shield includes:

a balloon disposed about the exterior of said probe;

a conduit communicated to said balloon on said probe; and, means for expanding and contracting said balloon from through said conduit relative to said probe whereby said shield can be expanded upon insertion to said operating site.

12. The apparatus of claim 9 and wherein said means for supplying includes:

means for supplying lasing energy to said conduit; and, said conduit is a fiber.

13. The apparatus of claim 9 and including:

a suction conduit within said probe, said suction conduit protruding from the opening of said probe to a location distal to optical viewing device; and, means for providing suction to said suction conduit.

14. The apparatus of claim 9 and wherein said probe includes a pistol-type grip at one end and said opening at said opposite end, and said probe is rotatable with respect to said grip.

15. The apparatus of claim 9 and wherein:

means for moving said energy conduit with respect to said opening in said probe whereby said conduit can be moved with respect to said view of said optical viewing device.

16. The apparatus of claim 15 and wherein said moving means includes:

means for moving said conduit in and out of said probe.

17. The apparatus of claim 15 and wherein said means for moving includes:

means for steering said conduit with respect to said probe.

18. A probe apparatus for surgery in an operating site having narrow substantially non manipulable entrance confines inhibiting side-to-side motion of said probe comprising:

a probe having a closed blunt non dissecting tip at a distal end, said blunt non dissecting tip having means for creating a space between tissues in the body of sufficient dimension to facilitate the surgery without interference from collapse of the tissues about the probe;

said probe defining at least one interior conduit having an opening at said means for defining a space;

a suction entrance defined in said space;

an optical viewing device within said probe, said optical viewing device providing visualization of into said space behind said closed blunt non dissecting tip of said probe for providing a field of view at said end of said probe;

a non penetrating conduit for energy discharge for transection, incision or treatment at said operating site within said probe, said conduit protruding to the suction entrance at said end of said probe and terminating in said field of view of said optical viewing device for the discharge of said energy;

means for supplying energy to said non penetrating conduit for energy discharge for transection, incision or treatment at said operating site; and means for manipulating said non penetrating conduit for energy discharge for transection, incision or treatment with respect to said end of said probe overlying said suction entrance in the view of said optical device at said operating site.

19. The apparatus of claim 18 and wherein:

means for cleaning said non penetrating conduit for energy discharge for transection, incision or treatment is disposed at said end of said probe.

20. The apparatus of claim 18 and including:

means for moving said energy conduit in and out of said probe.

21. The apparatus of claim 18 and wherein said means for moving includes:

means for steering said optical device with respect to said probe.

22. The apparatus of claim 18 and wherein said means for supplying includes:

means for supplying lasing energy to said conduit; and, said conduit is an fiber.

23. The apparatus of claim 18 and wherein said probe includes a pistol-type grip at one end and said opening at said opposite end.

24. The apparatus of claim 18 and wherein said means for defining a space behind said blunt non dissecting tip includes:

an expansible and contractible shield mounted to said probe, said shield moveable between a collapsed disposition conformed along side of said probe to an expanded disposition with respect to the side of said probe whereby said shield may be collapsed with respect to said probe during insertion and expanded when said shield is at or creating said operating site to create a space; and means for expanding and contracting said shield attached to said probe.

25. The apparatus of claim 24 and wherein said shield comprises:

a flexible mesh structure disposed about the exterior of said probe;

means for attaching a first portion of said flexible mesh structure at a first location on said probe;

means for attaching a second portion of said flexible mesh structure to a reciprocating portion of said probe whereby upon relative movement between said reciprocating portion of said probe and said first location on said probe said flexible mesh structure expands and contracts about said probe.

26. The apparatus of claim 24 and wherein said shield includes:

a balloon disposed about the exterior of said probe;

a conduit communicated to said balloon on said probe; and, means for expanding and contracting said balloon from through said conduit relative to said probe whereby said shield can be expanded upon insertion to said operating site.

* * * * *